United States Patent
Fink et al.

(10) Patent No.: US 10,271,720 B2
(45) Date of Patent: Apr. 30, 2019

(54) INTRAORAL IMAGING ILLUMINATION APPARATUS

(71) Applicant: 3M INNOVATIVE PROPERTIES COMPANY, St. Paul, MN (US)

(72) Inventors: Johannes Fink, Bergheim (DE); Guenter Zilligen, Grevenbroich (DE); David M. Rudek, Duesseldorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/127,622

(22) PCT Filed: Mar. 25, 2015

(86) PCT No.: PCT/US2015/022361
§ 371 (c)(1),
(2) Date: Sep. 20, 2016

(87) PCT Pub. No.: WO2015/148593
PCT Pub. Date: Oct. 1, 2015

(65) Prior Publication Data
US 2017/0172403 A1    Jun. 22, 2017

(30) Foreign Application Priority Data

Mar. 26, 2014    (EP) .................................... 14161782

(51) Int. Cl.
*A61B 1/247*    (2006.01)
*A61B 1/00*    (2006.01)
(Continued)

(52) U.S. Cl.
CPC .......... *A61B 1/247* (2013.01); *A61B 1/00101* (2013.01); *A61B 1/00105* (2013.01);
(Continued)

(58) Field of Classification Search
USPC ........................................................... 433/29
See application file for complete search history.

(56) References Cited

U.S. PATENT DOCUMENTS 5,306,144 A * 4/1994 Hibst .................. A61B 5/0088
356/317
6,263,234 B1 * 7/2001 Engelhardt .......... A61B 5/0088
600/476
(Continued)

FOREIGN PATENT DOCUMENTS

DE          9004995        9/1991
JP       2003-315150      11/2003
(Continued)

OTHER PUBLICATIONS

International Search Report for PCT International Application No. PCT/US2015/022361, dated Jun. 18, 2015, 3 pages.

*Primary Examiner* — Nicholas D Lucchesi
*Assistant Examiner* — Shannel N Wright (57) ABSTRACT

The present invention provides an intraoral imaging and illumination apparatus comprising a rear portion and a front portion removably connected to the rear portion. The front portion is formed as a light guide. The rear portion comprises an imaging device and an illumination device. The illumination device is adapted to couple light into the front portion and towards a leading end of the front portion opposite the rear portion so as to illuminate a first object. The imaging device is adapted to image the first object.

16 Claims, 7 Drawing Sheets

(51) Int. Cl.
*A61B 1/04* (2006.01)
*A61B 1/07* (2006.01)
*A61B 1/24* (2006.01)
*A61B 1/06* (2006.01)

(52) U.S. Cl.
CPC .......... *A61B 1/00165* (2013.01); *A61B 1/042* (2013.01); *A61B 1/063* (2013.01); *A61B 1/0669* (2013.01); *A61B 1/0684* (2013.01); *A61B 1/07* (2013.01); *A61B 1/24* (2013.01)

(56) References Cited

U.S. PATENT DOCUMENTS

| | | | | |
|---|---|---|---|---|
| 6,276,934 B1* | 8/2001 | Rakocz | ................ | A61B 1/247 433/29 |
| 6,384,917 B1* | 5/2002 | Fradkin | .................... | G01J 3/02 356/402 |
| 7,270,543 B2* | 9/2007 | Stookey | ................ | A61B 1/247 433/215 |
| 2003/0107652 A1* | 6/2003 | Williams | ........... | A61B 1/00177 348/207.99 |
| 2004/0117052 A1* | 6/2004 | Geng | ................ | A61B 1/00142 700/117 |
| 2004/0156626 A1* | 8/2004 | Thoms | ................ | A61B 1/0051 396/17 |
| 2004/0218039 A1* | 11/2004 | Cooper | ................... | A61B 1/05 348/66 |
| 2005/0090749 A1* | 4/2005 | Rubbert | ............ | A61B 1/00193 600/473 |
| 2005/0287490 A1* | 12/2005 | Stookey | ................ | A61B 1/247 433/29 |
| 2006/0292518 A1* | 12/2006 | Lee | ....................... | A61B 1/247 433/29 |
| 2008/0063998 A1* | 3/2008 | Liang | ................... | A61B 1/0638 433/29 |
| 2010/0157019 A1* | 6/2010 | Schwotzer | .............. | A61B 1/24 348/46 |
| 2010/0253773 A1* | 10/2010 | Oota | ........................ | A61B 1/24 348/77 |
| 2011/0221879 A1* | 9/2011 | Schmidt | ................ | A61B 1/247 348/77 |
| 2013/0135716 A1 | 5/2013 | Sataka | | |
| 2013/0189641 A1* | 7/2013 | Perfect | ............... | A61B 1/00089 433/29 |
| 2013/0236850 A1* | 9/2013 | Wu | .................... | A61B 1/00172 433/29 |
| 2014/0017625 A1* | 1/2014 | Liu | ........................ | A61B 1/042 433/29 |
| 2015/0010878 A1* | 1/2015 | Seibel | .................. | G01N 21/645 433/27 |
| 2015/0018613 A1* | 1/2015 | Hollenbeck | ........ | A61B 1/00096 600/109 |
| 2015/0029309 A1* | 1/2015 | Michaeli | ............ | G02B 21/0028 348/46 |
| 2015/0164335 A1* | 6/2015 | Van Der Poel | ...... | A61C 9/0053 433/29 |
| 2015/0250572 A1* | 9/2015 | Gramann | ............. | A61B 1/0684 433/29 |

FOREIGN PATENT DOCUMENTS

| | | |
|---|---|---|
| JP | 2008-173143 | 7/2008 |
| JP | 2012-011149 | 1/2012 |
| WO | WO 1999-042054 | 8/1999 |
| WO | WO 2004-021915 | 3/2004 |
| WO | WO 2009-139110 | 11/2009 |
| WO | WO 2013-025688 | 2/2013 |

* cited by examiner

INTRAORAL IMAGING ILLUMINATION APPARATUS

TECHNICAL FIELD

The present invention relates to an intraoral imaging and illumination apparatus for dental applications.

BACKGROUND

Dentists routinely rely on a number of different electronic tools. Among these electronic tools are intraoral cameras for inspection, medical documentation and patient visualization of planned medical procedures and their results. Low cost intraoral cameras with relatively poor imaging performance caused by distortions like strong cushion effects etc. start at a few hundred dollars. Top models with different focal length for both close-up as well as large area imaging with good image quality can reach several thousand dollars. The low-cost solutions position the camera chip directly at the tip of the device. In more sophisticated designs, a 45° prism or mirror reflects light towards the imager, located further along the device's longitudinal axis. This implementation generally achieves a better imaging performance as the increased optical path inside the device allows for a more complex lens design. However, as already mentioned, this typically results in higher parts and manufacturing costs.

Regardless of the position of the camera chip, known intraoral cameras combine camera chip, illumination LEDs and imaging optics in a single, sealed housing which is usually made from plastics. It is not possible to disconnect the front section which is in contact with the patient's mouth from the parts containing the electronics. Hence, current intraoral cameras can only be cleaned by dipping/wiping them in/with a cleaning agent. For additional protection, a single-use plastic cover can be slipped over the device head.

SUMMARY

Summarizing the above, the intraoral cameras made of one piece are difficult to clean which involves hygienic problems. Furthermore, the front section which comes into contact with the patient's mouth and which includes part of the electronic and or optical constructional members may not be disposed after use and, therefore, also has to be cleaned in a difficult manner.

Accordingly, the present invention is directed to overcoming the above problems. More particularly, the present invention is directed to provide an intraoral imaging and illumination apparatus which is simple in construction and has improved hygienic characteristics.

The present invention provides an intraoral imaging and illumination apparatus, comprising a rear portion and a front portion removably connected to the rear portion, wherein the front portion is formed as a light guide, the rear portion comprises an imaging device and an illumination device, wherein the illumination device is adapted to couple light into the front portion and towards a leading end of the front portion opposite the rear portion so as to illuminate a first object, wherein the imaging device is adapted to image the first object.

As the imaging device and the illumination device, which represent the essential electronic constructional members of the intraoral imaging and illumination apparatus, are arranged at the rear portion, the front portion is free of any essential electronic constructional members. Therefore, the front portion may be cleaned in an easy manner or may even be disposed after use. Further, as the front portion is formed as a light guide, light may be guided to a location of interest such as the first object even if the first object is located away from the rear portion. For example, the first object may be teeth of a patient. Light reflected by the first object may be imaged with an improved quality as the first object is illuminated by the illumination device.

The imaging device and the illumination device may be disposed within the rear portion. With other words, the imaging device and the illumination device may be located at the interior of the rear portion. Accordingly, the intraoral imaging and illumination apparatus may be designed in a compact manner.

The imaging device may comprise a camera. Accordingly, it is possible to image the first object with one or more images or even with a video.

The front portion may be adapted to reflect light coupled into the front portion. Accordingly, it is possible to guide light even in an angled manner to the first object and vice versa. With other words, this arrangement allows to guide light emitted by the illumination device to the first object and to guide light reflected from the first object not only in a direct manner but in an indirect manner.

The rear portion may define a first longitudinal axis. For example, the rear portion may be substantially tube-shaped or cylindrical, wherein the tube or cylindrical shape defines the first longitudinal axis. The imaging device or the illumination device may be axially arranged with respect to the first longitudinal axis. Thus, the first longitudinal axis runs through the imaging device or illumination device. The imaging device or the illumination device may be arranged offset with respect to the first longitudinal axis. For example, the imaging device or the illumination device may be arranged radially with respect to the first longitudinal axis. With other words, one of the imaging device and the illumination device may be axially arranged with respect to the first longitudinal axis and the other one of imaging device and the illumination device, which is not axially arranged with respect to the first longitudinal axis, may be arranged offset with respect to the first longitudinal axis such as radially with respect to the first longitudinal axis.

The intraoral imaging and illumination may further comprise a beam splitter disposed within the rear portion. The beam splitter may be adapted to split light emitted by the illumination device and incident thereon into a first fraction and a second fraction. The beam splitter is further adapted to reflect the first fraction of the light towards the front portion and to transmit the second fraction of the light towards a second object different from the first object. This arrangement allows to illuminate two different objects at the same time, preferably under the same illumination conditions. For example, the second object may be located within the rear portion. The second object may be a colour standard or a palette of colour references. Accordingly, it is possible for a user of the intraoral imaging and illumination apparatus to observe the first object and to compare it with the second object. For example, the user may be a dentist which observes teeth of a patient as the first object and compares the colour of the teeth with a colour standard as the second object. The imaging device may be adapted to image the second object. For example, the beam splitter may be adapted to deflect light reflected by the second object towards the imaging device. Therefore, the user may image two different objects.

The intraoral imaging and illumination apparatus may be further comprise a focusing device disposed within the rear portion. The focusing device may be disposed between the imaging device and the beam splitter. Thereby, back reflections may be prevented from falling onto the imaging device.

The intraoral imaging and illumination may further comprise a dichroic mirror disposed within the rear portion. The dichroic mirror may be adapted to reflect at least 70% of light having a wavelength smaller than 500 nm and may be adapted to transmit at least 75% of light having a wavelength greater than 500 nm. Thereby, the light coupling efficiency may be increased.

The intraoral imaging and illumination apparatus may further comprise a focusing device disposed within the rear portion. The focusing device may be disposed between the imaging device and the dichroic mirror. Thereby, back reflections may be prevented from falling onto the imaging device and the light coupling efficiency may be increased.

The front portion may comprise a proximal section facing the rear portion and a distal section facing away from the rear portion. The proximal section and the distal section may be angled relative to one another. The front portion may comprise a reflecting device disposed at a transition from the proximal section to the distal section. Thereby, light may be guided to positions not arranged on a direct line but in an indirect manner.

The proximal section may define a second longitudinal axis. The first longitudinal axis and the second longitudinal axis may overlap when the front portion is connected to the rear portion. This arrangement provides an elongation of the rear portion by the proximal section.

The front portion may comprise a rear end facing the rear portion. A first optical interface may be arranged at the rear end. The first optical interface may be tilted with respect to the second longitudinal axis. Thereby, back reflections may be prevented from falling onto the imaging device.

The distal section may define a third longitudinal axis. The third longitudinal axis may be angled with respect to the second longitudinal axis. Thereby, light may be guided to positions not arranged on a direct line but in an indirect manner.

A second optical interface may be arranged at the leading end of the front portion. The second optical interface may be tilted with respect to the third longitudinal axis. Thereby, back reflections may be prevented from falling onto the imaging device.

The first optical interface and/or the second optical interface may be coated with an anti-reflection coating. Thereby, back reflections may be prevented from falling onto the imaging device.

The illumination device may comprise at least one light source. For example, the illumination device may comprise at least one LED or laser. The at least one LED or laser may be arranged coaxially with respect to the imaging device. This arrangement allows to reliably illuminate the first object without any shadows. The intraoral imaging and illumination may further comprise at least one collimating device adapted to collimate light emitted from the at least one LED or laser. Thereby, the light coupling efficiency may be increased. The at least one LED or laser may be tilted with respect to a central axis. Thereby, the light coupling efficiency may be further increased.

The front portion may be a hollow light guide comprising an inner surface adapted to reflect light. This arrangement may be manufactured with decreased costs.

Alternatively, the light guide may be a solid light guide adapted to reflect light. Thereby, the light coupling efficiency may be increased. The solid light guide may be made at least partially of plastics or glass. The solid light guide may comprise a rectangular cross-section. This arrangement may be manufactured with decreased costs.

The light guide may comprise light coupling elements tilted with respect to a central axis. Thereby, the light coupling efficiency may be increased.

A light guide in the sense of the present invention is any constructional member in the form of a hollow body or solid body that is adapted to guide light to a predetermined location such as an object to be imaged.

An imaging device in the sense of the present invention is any device that is adapted to image an object. For example, the imaging device may image an object using a camera.

An illumination device in the sense of the present invention is any device adapted to emit light. For example, the illumination device may emit light using a light source such as a LED or laser.

A beam splitter in the sense of the present invention is an optical device that is adapted to split a beam of light into at least two beams.

A dichroic mirror in the sense of the present invention is a mirror that is adapted to selectively pass light of a small range of colours by reflecting other colours. Usually, a dichroic mirror is characterized by the colour(s) of light that it reflects rather than the colour(s) it passes.

A collimating device in the sense of the present invention is a device that narrows a beam of rays. "To narrow" can mean either to cause of directions of motions to become more aligned in specific directions, such as collimated or parallel, or to cause the spatial cross-section of the beam to become smaller.

An arrangement offset with respect to an axis in the sense of the present invention is an arrangement, wherein the respective element is not located on the axis but is spaced apart therefrom. Thus, the term "offset" includes a lateral displacement such as parallel but off-axis placement and an angular change such as a rotation in a three dimensional space.

An optical interface in the sense of the present invention is any surface adapted to transmit light without any substantial optical losses. Such an optical interface may be made of glass or any other transparent material and it could also be a surface of a solid light guide.

Summarizing, particular embodiments of the present invention are:

1. Intraoral imaging and illumination apparatus, comprising a rear portion and a front portion removably connected to the rear portion, wherein
   the front portion is formed as a light guide,
   the rear portion comprises an imaging device and an illumination device, wherein the illumination device is adapted to couple light into the front portion and towards a leading end of the front portion opposite the rear portion so as to illuminate a first object, wherein the imaging device is adapted to image the first object.
2. Intraoral imaging and illumination apparatus according to the preceding embodiment, wherein the imaging device and the illumination device are disposed within the rear portion.
3. Intraoral imaging and illumination apparatus according to any preceding embodiment, wherein the imaging device comprises a camera.
4. Intraoral imaging and illumination apparatus according to any preceding embodiment, wherein the front portion is adapted to reflect light coupled into the front portion.
5. Intraoral imaging and illumination apparatus according to any preceding embodiment, wherein the rear portion defines a first longitudinal axis, wherein the imaging device or the illumination device is axially arranged with respect to the first longitudinal axis.
6. Intraoral imaging and illumination apparatus according to the preceding embodiment, wherein the imaging device or the illumination device is arranged offset with respect to the first longitudinal axis.
7. Intraoral imaging and illumination apparatus according to embodiment 5 or 6, wherein illumination device is arranged radially with respect to the first longitudinal axis.
8. Intraoral imaging and illumination apparatus according to any preceding embodiment, further comprising a beam splitter disposed within the rear portion, wherein the beam splitter is adapted to split light emitted by the illumination device and incident thereon into a first fraction and a second fraction, wherein the first fraction of the light is reflected towards the front portion and the second fraction of the light is transmitted towards a second object different from the first object.
9. Intraoral imaging and illumination apparatus according to the preceding embodiment, wherein the second object is located within the rear portion.
10. Intraoral imaging and illumination apparatus according to embodiment 8 or 9, wherein the second object is a colour standard or a palette of colour references.
11. Intraoral imaging and illumination apparatus according to any one of embodiments 8 to 10, wherein the imaging device is adapted to image the second object.
12. Intraoral imaging and illumination apparatus according to any one of embodiments 8 to 11, wherein the beam splitter is adapted to deflect light reflected by the second object towards the imaging device.
13. Intraoral imaging and illumination apparatus according to any one of embodiments 8 to 12, further comprising a focusing device disposed within the rear portion.
14. Intraoral imaging and illumination apparatus according to the preceding embodiment, wherein the focusing device is disposed between the imaging device and the beam splitter.
15. Intraoral imaging and illumination apparatus according to any one of embodiments 1 to 7, further comprising a dichroic mirror disposed within the rear portion.
16. Intraoral imaging and illumination apparatus according to the preceding embodiment, wherein the dichroic mirror is adapted to reflect at least 70% of light having a wavelength smaller than 500 nm and is adapted to transmit at least 75% of light having a wavelength greater than 500 nm.
17. Intraoral imaging and illumination apparatus according to embodiment 15 or 16, further comprising a focusing device disposed within the rear portion.
18. Intraoral imaging and illumination apparatus according to the preceding embodiment, wherein the focusing device is disposed between the imaging device and the dichroic mirror.
19. Intraoral imaging and illumination apparatus according to any preceding embodiment, wherein the front portion comprises a proximal section facing the rear portion and a distal section facing away from the rear portion, wherein the proximal section and the distal section are angled relative to one another.
20. Intraoral imaging and illumination apparatus according to the preceding embodiment, wherein the front portion comprises a reflecting device disposed at a transition from the proximal section to the distal section.
21. Intraoral imaging and illumination apparatus according to the preceding embodiment, wherein the proximal section defines at a second longitudinal axis, wherein the first longitudinal axis and the second longitudinal axis overlap when the front portion is connected to the rear portion.
22. Intraoral imaging and illumination apparatus according to the preceding embodiment, wherein the front portion comprises a rear end facing the rear portion, wherein a first optical interface is arranged at the rear end, wherein the first optical interface is tilted with respect to the second longitudinal axis.
23. Intraoral imaging and illumination apparatus according to any one of embodiments 20 to 22, wherein the distal section defines a third longitudinal axis, wherein the third longitudinal axis is angled with respect to the second longitudinal axis.
24. Intraoral imaging and illumination apparatus according to the preceding embodiment, wherein a second optical interface is arranged at the leading end of the front portion, wherein the second optical interface is tilted with respect to the third longitudinal axis.
25. Intraoral imaging and illumination apparatus according to any one of embodiments 22 to 24, wherein the first optical interface and/or the second optical interface are coated with an anti-reflection coating.
26. Intraoral imaging and illumination apparatus according to any preceding embodiment, wherein the illumination device comprises at least one light source.
27. Intraoral imaging and illumination apparatus according to any preceding embodiment, wherein the illumination device comprises at least one LED or laser.
28. Intraoral imaging and illumination apparatus according to the preceding embodiment, wherein the at least one LED or laser is arranged coaxially with respect to the imaging device.
29. Intraoral imaging and illumination apparatus according to the preceding embodiment, wherein the at least one LED or laser is tilted with respect to a central axis.
30. Intraoral imaging and illumination apparatus according to embodiment 28 or 29, further comprising at least one collimating device adapted to collimate light emitted from the at least one LED or laser.
31. Intraoral imaging and illumination apparatus according to any preceding embodiment, wherein the front portion is a hollow light guide comprising an inner surface adapted to reflect light.
32. Intraoral imaging and illumination apparatus according to any one of embodiments 1 to 30, wherein the light guide is a solid light guide adapted to reflect light.
33. Intraoral imaging and illumination apparatus according to the preceding embodiment, wherein the solid light guide is made at least partially of plastics or glass.
34. Intraoral imaging and illumination apparatus according to embodiment 32 or 33, wherein the solid light guide comprises a rectangular cross-section.
35. Intraoral imaging and illumination apparatus according to any of embodiments 31 to 34, wherein the light guide comprises light coupling elements tilted with respect to a central axis.

BRIEF DESCRIPTION OF THE DRAWINGS

By way of example, an intraoral imaging illumination apparatus in accordance with the invention will now be described with reference to the accompanying drawings in which.

DETAILED DESCRIPTION

Figure 1:
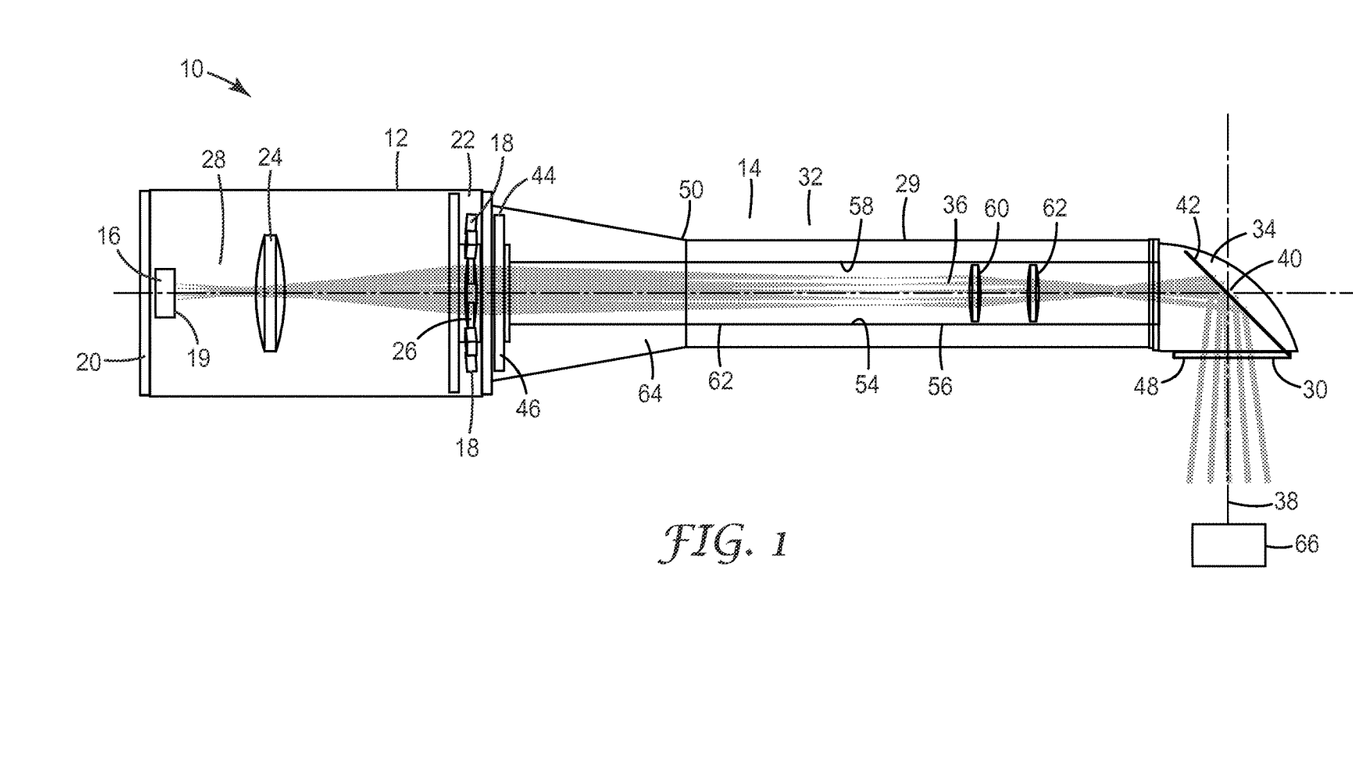
FIG. 1 shows a cross-sectional view of an intraoral imaging and illumination apparatus according to a first embodiment of the present invention.

FIG. 1 shows a cross-sectional view of an intraoral imaging and illumination apparatus 10 according to a first embodiment of the present invention. The intraoral imaging and illumination apparatus 10 shown in FIG. 1 is of a type for use in the dental field. Particularly, the intraoral imaging and illumination apparatus 10 is adapted to be used in the mouth of a patient.

The intraoral imaging and illumination apparatus 10 comprises a rear portion 12 and a front portion 14 removably connected to the rear portion 12. For example, the front portion 14 may be connected to the rear portion 12 by means of a snap-fit mechanism or the like.

The rear portion 12 comprises an imaging device 16 and illumination device 18. Particularly, the imaging device 16 and the illumination device 18 are disposed within the rear portion 12. The imaging device 16 comprises a camera 19. The illumination device 18 comprises at least on light source. For example, the light source may be at least one LED. Alternatively, the light source may be at least one laser. The imaging device 16 may be arranged at or close to a first end 20 of the rear portion 12 which faces away from the front portion 14. The illumination device 18 may be arranged at or close to a second end 22 of the rear portion 12 facing the front portion 14. A first lens 24 and a second lens 26 are arranged between the imaging device 16 and the illumination device 18. At least one of the first lens 24 and the second lens 26 is moveable. For example, the first lens 24, which is arranged closer to the imaging device 16, is moveable.

As can be further taken from FIG. 1, the rear portion 12 is substantially tube-shaped or cylindrical. For example, the rear portion comprises a length of 35 mm and a diameter of 20 mm. Thus, the rear portion 12 defines a first longitudinal axis 28 along which the rear portion 12 extends. The first lens 24 is axially moveable with respect to the first longitudinal axis 28. The imaging device 16 is axially arranged with respect to the first longitudinal axis 28. The illumination device 18 is arranged offset with respect to the first longitudinal axis 28. For example, the illumination device 18 comprises a plurality of LEDs which are arranged coaxially with respect to the first longitudinal axis 28. For example, the LEDs of the illumination device 18 are arranged circularly around the first longitudinal axis 28 representing the optical path of the imaging device 16.

The front portion 14 is formed as a light guide 29. The light guide 29 is a hollow light guide as will be explained in further detail below. The front portion 14 is substantially tube-shaped or cylindrical. For example, the rear portion comprises a length of 80 mm and a diameter of 12 mm. The front portion 14 comprises a leading end 30 opposite the rear portion 12. More particularly, the front portion 14 comprises a proximal section 32 facing the rear portion 12 and a distal section 34 facing away from the rear portion 12. The proximal section 32 and the distal section 34 are angled relative to one another. For example, the proximal section 32 and the distal section 34 form an angle of about 90° relative to one another. The angle between the proximal section 32 and the distal section 34 may be determined as an angle between a second longitudinal axis 36 defined by the proximal section 32 and a third longitudinal axis 38 defined by the distal section 34. Accordingly, the third longitudinal axis 38 is angled with respect to the second longitudinal axis 36. The first longitudinal axis 28 and the second longitudinal axis 36 overlap when the front portion 14 is connected to the rear portion 12.

The front portion 14 comprises a reflecting device 40 disposed at a transition 42 from the proximal section 32 to the distal section 34. The reflecting device 40 may be a mirror. Further, the front portion 14 comprises a rear end 44 facing the rear portion 12. A first optical interface 46 is arranged at the rear end 44. The first optical interface may be a glass window. A second optical interface 48 is arranged at the leading end 30 of the front portion 14. The second optical interface 48 may also be a glass window. The first optical interface 46 and/or the second optical interface 48 are coated with an anti-reflection coating. It is to be noted that the first optical interface 46 and the second optical interface 48 are transparent for light. The first optical interface 46 and the second optical interface 48 are used for hermetically covering the interior of the front portion 14. In order to hermetically cover the interior of the rear portion 12, it is explicitly stated that the first optical interface 46 or a third optical interface (not shown in detail) may be arranged at the second end 22 of the rear portion 12.

The proximal section 32 of the front portion 14 is formed by two hollow tubes 50, 52 stacked into one another. With other words, the proximal section 32 comprises an outer tube 50 and an inner tube 52. The outer tube 50 has a mirrored inner surface 54 and the inner tube 52 has a mirrored outer surface 56. With other words, the front portion 14 is a hollow light guide 29 comprising an inner surface 54 adapted to reflect light. An inner surface 58 of the inner tube 52 may be coated for absorbing light to prevent stray light from falling onto the imaging device 16. Ideally the reflecting surfaces 54, 56 should have a reflectivity as high as possible. For example, instead of aluminium mirror surfaces, which have a reflectivity of about 95%, ESR films, which have a reflectivity of about 99%, may be used. This easily doubles the light output. A third lens 60 and a fourth lens 62 are arranged within the front portion 14. More particularly, the third lens 60 and the fourth lens 62 are arranged within the inner tube 52 of the proximal section 32 of the front portion 14. It is to be noted that the outer tube 50 and the inner tube 52 are spaced apart from one another by a gap 64

The illumination device 18 is adapted to couple light into the front portion 14 and towards the leading end 30 of the front portion 14 so as to illuminate a first object 66 such as a tooth of the patient. Accordingly, the first object 66 is located outside the intraoral imaging and illumination apparatus 10. The light may be polymerization light. In this case, the illumination device 18 comprises UV/blue lamps. These bright UV/blue lamps are used to solidify dental fillings after application. More particularly, light entering the front portion 14 through the first optical interface 46 is coupled into the proximal section 32 within the gap 64 between the outer tube 50 and the inner tube 52. The light is guided towards the reflecting device 40. For example, the light may be reflected at the mirrored inner surface 54 and the mirrored outer surface 56 so as to be guided towards the reflecting device 40 by means of multiple reflections at the mirrored inner surface 54 and the mirrored outer surface 56. Then, the light is reflected at the reflecting device 40 towards the leading end 30. For example, the reflecting device 40 may be arranged so as to deflect light at an angle of about 90°. The light then exits the front portion 14 through the second window glass 48 and is incident on the first object 66. The distal section 34 may be tapered which facilitates coupling of the light of the LEDs to a relatively small-diameter hollow light guide 29.

Light reflected from the first object 66 enters the front portion 14 through the second window glass 48 and is reflected off the reflecting device 40 towards the rear end 44. More particularly, the light is reflected off the reflecting device 40 into the inner tube 52 of the proximal section 32. The third lens 60 and the fourth lens 62 focus the light towards the rear end 44 and the rear portion 12. The light then exits the front portion 14 through the first optical interface 46 and enters the rear portion 12. The first lens 24 and the second lens 26 further focus the light onto the imaging device 16. Accordingly, the first lens 24 and the second lens 26 serve as a focusing device 68 disposed within the rear portion 12. Focusing onto different objects is accommodated by moving for example the first lens 24 along the first longitudinal axis 28.

With other words, the apparatus 10 allows to combine an intraoral camera and polymerization light with a removable front portion 14. As such it offers said camera and illumination functionality with a fully passive device tip, i.e. a removable several centimeter long front portion 14 without any electronic equipment. The problem of guiding the polymerization light towards the first object 66 is solved by guiding light emitted from the illumination device 18 within a closed tube-shaped front portion 14, which offer superior illumination homogeneity with respect to rivalling solutions. All in all the proposed apparatus 12 has the major benefit that the dentist can remove the front portion 14 for thorough cleaning/sterilization, offering an altogether different level of hygiene compared to the known devices. The placement of high power LEDs outside of the patient's mouth furthermore allows a better heat management, as the dimensions of the heat sinks are not constrained by the small form factor required by the mouth piece. A third benefit of this solution is the facilitated certification, as the patient does not get into contact with active electronic equipment. The user can reduce the glare from the powerful light source by attaching a transparent yellow plastic sheet to the front portion 14. A simple control interface (not shown in detail) allows choosing different illumination durations.

Figure 2:
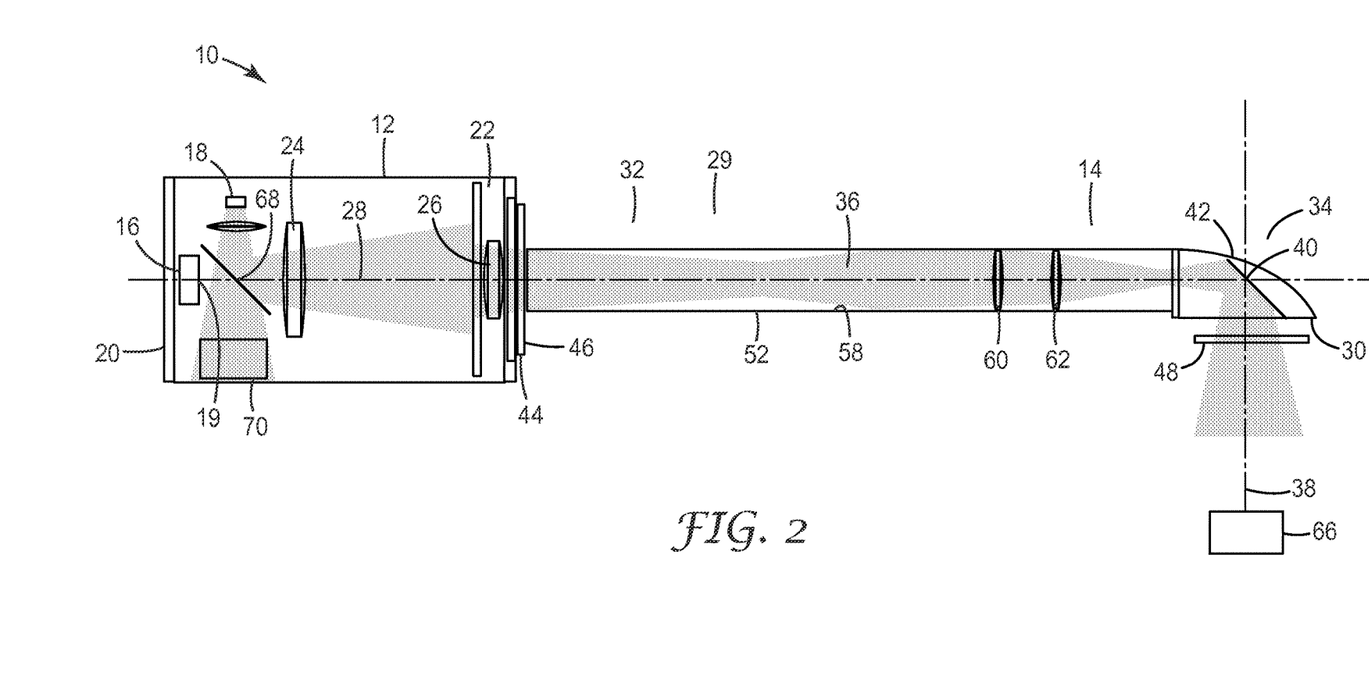
FIG. 2 shows a cross-sectional view of an intraoral imaging and illumination apparatus according to a second embodiment of the present invention.

FIG. 2 shows a cross-sectional view of an intraoral imaging and illumination apparatus 10 according to a second embodiment. Hereinafter, only differences from the first embodiment are described and like constructional members are indicated by like reference signs.

According to the second embodiment, the illumination device 18 is arranged offset with respect to the first longitudinal axis 28. More particularly, the illumination device 18 is radially arranged with respect to the first longitudinal axis 28. As with the intraoral imaging and illumination apparatus 10 according to the first embodiment, the imaging device 16 is axially arranged with respect to the first longitudinal axis 28.

The intraoral imaging and illumination apparatus 10 according to the second embodiment comprises a beam splitter 68. The beam splitter 68 is disposed within the rear portion 12. More particularly, the beam splitter 68 is disposed between the imaging device 16 and the first lens 24 if seen in an extension direction of the first longitudinal axis 28. Further, a second object 70 is located within the rear portion 12. The second object 70 is different from the first object 66. More particularly, the second object 70 is located opposite the illumination device 18 with the beam splitter 68 therebetween.

The beam splitter 68 is adapted to split light emitted by the illumination device 18 and incident thereon into a first fraction and a second fraction. The first fraction of the light is reflected towards the front portion 14. The second fraction of the light is transmitted towards the second object 70. With this construction, the imaging device 16 is adapted to image the second object 70. Particularly, the beam splitter 68 is adapted to deflect light reflected by the second object 70 towards the imaging device 16. It is explicitly stated, that the beam splitter 68 may be replaced by a semi-transparent mirror.

The intraoral imaging and illumination apparatus 10 according to the second embodiment allows to directly couple the first fraction of the light into the optical path of the imaging device 16. Thereby, the outer tube 50 of the proximal section 32 of the front portion 14 may be omitted and the proximal section 32 may comprise only the inner tube 52. Accordingly, in case the outer tube 50 is omitted, the diameter of the front portion 14 according to the second embodiment may be reduced if compared to front portion 14 of the first embodiment. For example, the diameter of the front portion 14 according to the second embodiment may be 6 mm instead of 12 mm according to the first embodiment.

The intraoral imaging and illumination apparatus 10 according to the second embodiment allows to image two different objects 66, 70. The first object 66 is illuminated by the first fraction of light and the second object 70 is illuminated by the second fraction of light. Particularly, the first fraction of light and light reflected from the first object 66 both propagate through the inner tube 52.

Figure 3:
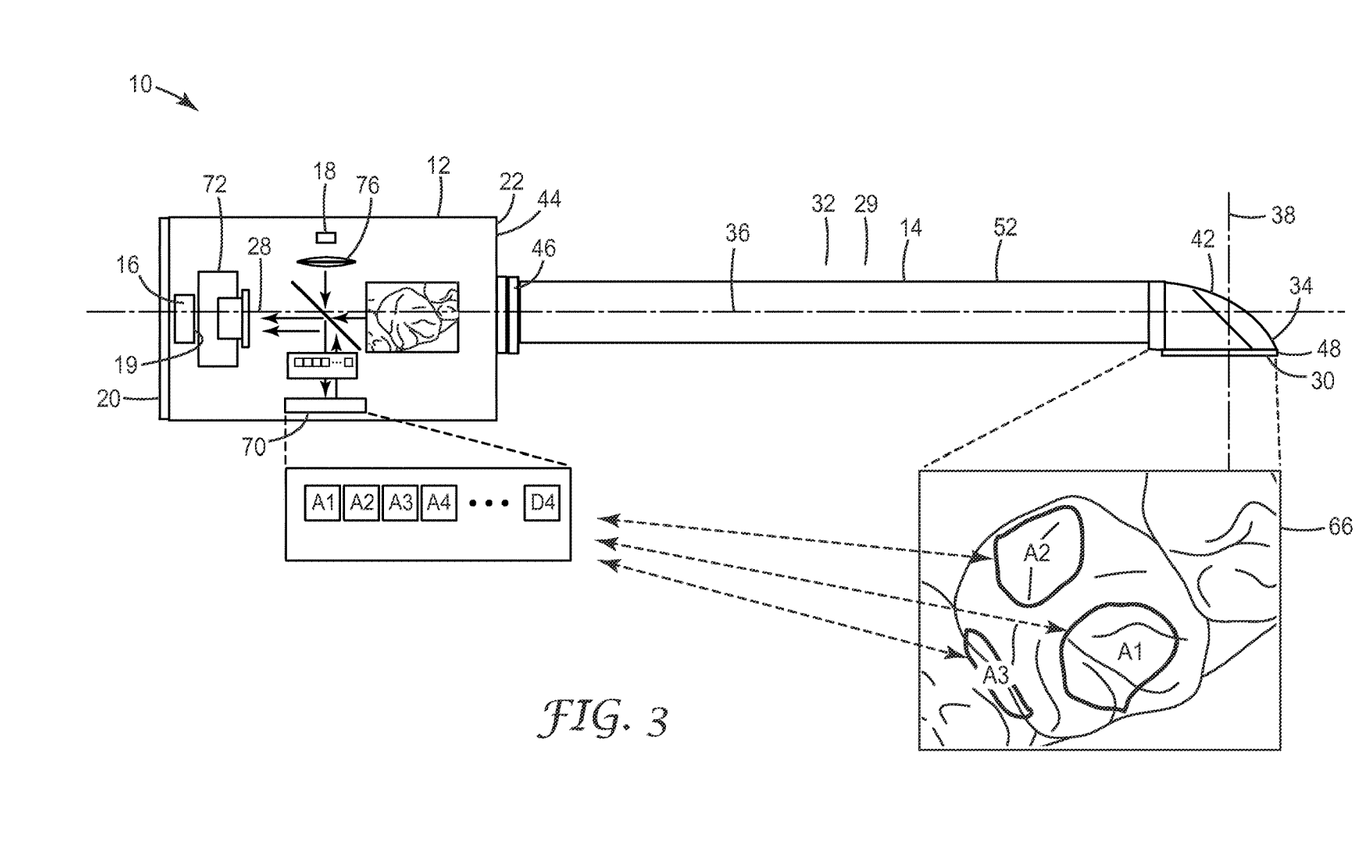
FIG. 3 shows a cross-sectional view of an intraoral imaging and illumination apparatus according to a third embodiment of the present invention.

FIG. 3 shows a cross-sectional view of an intraoral imaging and illumination apparatus 10 according to a third embodiment. Hereinafter, only differences from the first and second embodiments are described and like constructional members are indicated by like reference signs.

The intraoral imaging and illumination apparatus 10 of the third embodiment is substantially based on the second embodiment. According to the intraoral imaging and illumination apparatus 10 of the third embodiment, the second object 70 is a colour standard or a palette of colour references. The intraoral imaging and illumination apparatus 10 of the third embodiment further comprises focusing device 72. The focusing device 72 is disposed within the rear portion 12. More particularly, the focusing device 72 is disposed between the imaging device 16 and the beam splitter 68. The focusing device 72 replaces the first lens 24 and the second lens 26 used with the first and second embodiments. The focusing device 72 is a fast, small form-factor automated focusing unit. For example, the focusing device is a M3-F focus module available from New Scale Technologies, 121 Victor Heights Parkway Victor, N.Y. 14564, USA.

The intraoral imaging and illumination apparatus 10 of the third embodiment addresses the intrinsic need of colour/shade matching tools for a calibration step prior to the actual object evaluation in order to account for changing ambient conditions like temperature and lighting. It is proposed to integrate the second object 70 in form of the required colour standard into the rear portion 12 and shine the LED light on both the colour standard and the first object 66 simultaneously under the same illumination conditions. The focusing device 72 is able to quickly focus on the colour standard and back onto the first object 66 and thereby to increase the stability of a colour matching process. This ultimately leads to a system using a software algorithm for proposing colour values for certain image regions.

Colour or shade matching is a widely used technique covering applications such as digital printing, car painting and dental restoration. In all cases, the technique involves a calibration step prior to the measurement, requiring the user to target a reference object, which is often a diffuse white reflectance standard, prior to the actual colour measurement. In the field of dentistry, it is also customary to visually gauge a tooth's shade against a reference chart of e.g. 16 different shades. In many cases, the results vary strongly depending on the dentist's ability to perceive colours and to differentiate similar shades.

Particularly, the focusing device 72 is actually able to focus on objects placed inside the rear portion 12. In combination with the beam splitter 68, which is used to guide the LED light to the leading end 30, this allows to shift the focus from the first fraction of light of the beam splitter 68 to the second fraction of light. For example, it is possible to focus on the first object 66, e.g. a tooth in the patient's mouth, or alternatively on the second object 70, i.e. a colour standard or a palette of colour references. This colour palette could potentially even include or consist only of restorative material colours, thereby linking the colour evaluation hardware to consumable materials.

Accordingly, the intraoral imaging and illumination apparatus 10 of the third embodiment provides a multifunctional tool, which gives the dentist a recommendation about what colour a tooth has. It would make a separate calibration step or even the manual comparison against a colour standard, e.g. a tooth shaped plastic object positioned next to the tooth under evaluation, obsolete. It would potentially even allow to tailor the system's response, e.g. best colour matching result, to restorative materials. Thus, no manual referencing is necessary.

The intraoral imaging and illumination apparatus 10 of the third embodiment has two particular benefits. First, the focus adjustment happens very quickly, allowing multiple repetitive images of the first object 66 and the second object 70 to be taken. Secondly, both the first object 66 and the second object 70 are illuminated by the same light source. If the illumination device 18 is a built-in light source that is strong enough, effects of ambient light on for example exposed front teeth should be negligible.

Figure 4:
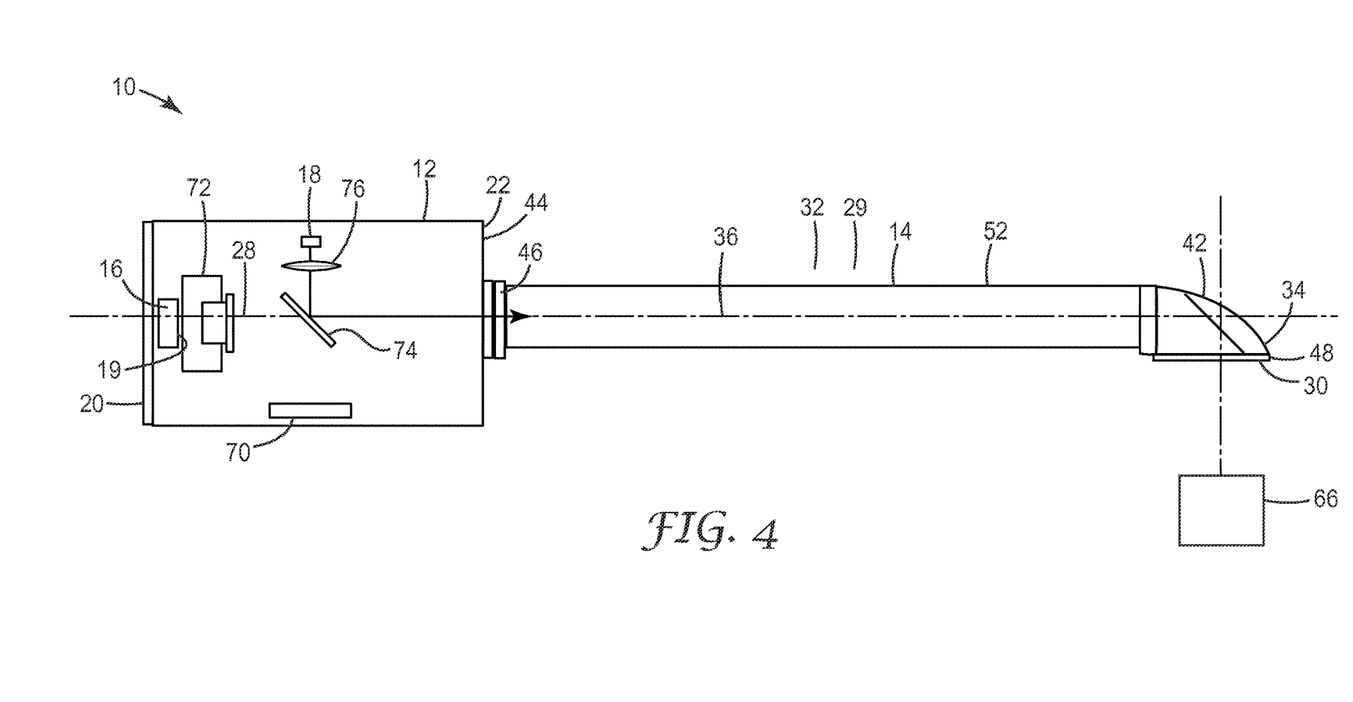
FIG. 4 shows a cross-sectional view of an intraoral imaging and illumination apparatus according to a fourth embodiment of the present invention.

FIG. 4 shows a cross-sectional view of an intraoral imaging and illumination apparatus 10 according to a fourth embodiment. Hereinafter, only differences from the previous embodiments are described and like constructional members are indicated by like reference signs.

The intraoral imaging and illumination apparatus 10 of the fourth embodiment is substantially based on the third embodiment. The intraoral imaging and illumination apparatus 10 of the fourth embodiment comprises a dichroic mirror 74. The dichroic mirror 74 is disposed within the rear portion 12. The dichroic mirror 74 replaces the beam splitter 68 used with the third embodiment. The dichroic mirror 74 is adapted to reflect at least 70% of light having a wavelength smaller than 500 nm and is adapted to transmit at least 75% of light having a wavelength greater than 500 nm.

Similar as the intraoral imaging and illumination apparatus 10 of the third embodiment, the intraoral imaging and illumination apparatus 10 of the fourth embodiment comprises the focusing device 72. The focusing device 72 is disposed within the rear portion 12. More particularly, the focusing device 72 is disposed between the imaging device 16 and the dichroic mirror 74. As the polymerization process requires blue light, it is proposed to use a blue reflecting dichroic mirror 74 that is required to couple the light of the illumination device 18 into the optical axis of the intraoral imaging and illumination apparatus 10.

The intraoral imaging and illumination apparatus 10 of the fourth embodiment may further comprise one collimating device 76 adapted to collimate light emitted from the illumination device 18. The collimating device 76 may be arranged between the illumination device 18 and the dichroic mirror 74. The collimating device 76 may be a collimating lens. For example, the collimating device 76 is adapted to collimate light emitted from at least one of the plurality of LEDs or lasers of the illumination device 18.

The intraoral imaging and illumination apparatus 10 of the fourth embodiment increases the light coupling efficiency if compared with the third embodiment. Particularly, the broadband beam splitter 68 of the third embodiment may comprise intrinsic losses of more than 25%. The wavelength-selective dichroic mirror 74 of the fourth embodiment may comprise intrinsic losses below 3% which allows to efficiently couple the polymerization light into the optical axis of the intraoral imaging and illumination apparatus 10.

In combination with a well collimated source like a laser diode or an LED with a custom collimator 76, the proposed dichroic mirror 74 increases the light guiding efficiency. For example, it is possible to generate a picture under polymerization light, i.e. blue light only, by using what little light still comes through the dichroic mirror 74. However, as the colour information is lost when using only blue light, a software conversion of the original image into a grey-scale version would give the doctor the necessary position feedback while discarding the colour information. Nevertheless, when using a white light source, e.g. LED, it is still possible to use the imager's white balancing to obtain limited colour information. The impact of the coloured mirror is even further reduced if an additional ambient light source, e.g. doctor's chair side lamp, can be used. Finally, it is also conceivable to combine the beam splitter 68 and the dichroic mirror 74, e.g. to move either one or the other component into the optical path, depending on the task at hand. If the doctor were to take a colour image or to visualize something under white light conditions with good colour representation, the beam splitter 68 could be used as a high light guiding efficiency and would not be critical. For polymerization applications, where it is necessary to almost fully use the LED's optical power, the dichroic mirror 74 would boost the light coupling efficiency. It is to be noted that the third lens 60 and the fourth lens 62 of the front portion 14 may be omitted.

Figure 5:
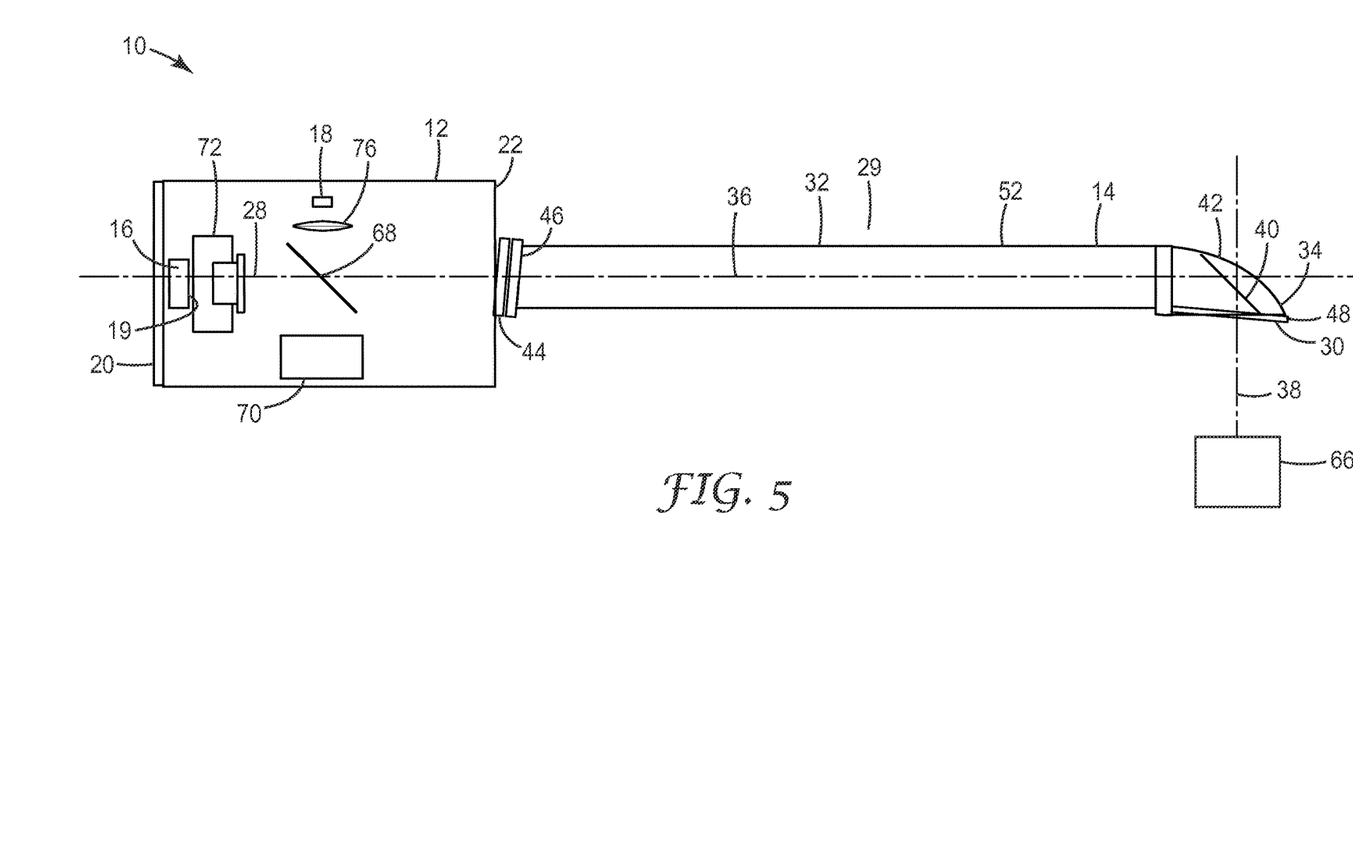
FIG. 5 shows a cross-sectional view of an intraoral imaging and illumination apparatus according to a fifth embodiment of the present invention.

FIG. 5 shows a cross-sectional view of an intraoral imaging and illumination apparatus 10 according to a fifth embodiment. Hereinafter, only differences from the previous embodiments are described and like constructional members are indicated by like reference signs.

The intraoral imaging and illumination apparatus 10 of the fifth embodiment is substantially based on the third embodiment. According to the intraoral imaging and illumination apparatus 10 of the fifth embodiment, the first optical interface 46 is tilted with respect to the second longitudinal axis 36. Further, the second optical interface 48 is tilted with respect to the third longitudinal axis 38. It is to be noted that the third lens 60 and the fourth lens 62 of the front portion 14 are preferably omitted as shown in FIG. 5.

Similar as the intraoral imaging and illumination apparatus 10 of the third embodiment, the intraoral imaging and illumination apparatus 10 of the fifth embodiment comprises the beam splitter 68 which is disposed within the rear portion 12. More particularly, the beam splitter 68 is disposed between the imaging device 16 and the first lens 24 if seen in an extension direction of the first longitudinal axis 28. Similar as the intraoral imaging and illumination apparatus 10 of the third embodiment, the intraoral imaging and illumination apparatus 10 of the fifth embodiment comprises the focusing device 72. The focusing device 72 is disposed within the rear portion 12. More particularly, the focusing device 72 is disposed between the imaging device 16 and the beam splitter 68.

The intraoral imaging and illumination apparatus 10 of the fifth embodiment may further comprise a collimating device 76 adapted to collimate light emitted from the illumination device 18. The collimating device 76 may be arranged between the illumination device 18 and the beam splitter 68. The collimating device 76 may be a collimating lens. For example, the collimating device 76 is adapted to collimate light emitted from at least one of the plurality of LEDs or lasers of the illumination device 18.

Thus, it is proposed to reduce the optical elements inside the removable front portion 14 to the absolute minimum, i.e. the front portion 14 has only the protective first and second optical interfaces 46, 48 at the leading end 30 and the rear end 44. Apart from reducing the number of reflective interfaces, this also has the benefit of reducing the costs for the removable front portion 14, which has to undergo harsh cleaning conditions and therefore might at some point need to be replaced.

As a consequence, all focusing and imaging optics for the imaging device 16 as well for the collimation of the LED illumination from the illumination device 18 are located in front of the beam splitter 68, i.e. the camera 19 of the imaging device and the focusing device 72 are located in front of the beam splitter 68 if seen in a direction from the rear portion 12 towards the front portion 14. For example, a conventional f=8 mm S-mount objective in combination with a piezo-driven focus module can handle the imaging process. It is possible to both focus on the first object 66 placed right in front of the leading end 30 of the removable front portion 14 as well as objects located very far away (infinity). Alternatively, the focusing can be done manually or even fully without transverse movement via an electrically focusable lens.

The fifth embodiment is advantageous in that the particular problem that each optical element (lens or glass plate) located behind the beam splitter 68 or dichroic mirror 74, i.e. along the optical axis in the direction of the intraoral imaging and illumination apparatus 10, will introduce back reflections is solved. These back reflections are generated at the air-glass interfaces of the optical elements and introduce image artefacts Finally, it is also proposed to additionally or alternatively apply a technique, which is often used to reduce back reflections in fibre optics. So-called angled-physical contact (APC) connectors use interfaces with a slight angle, e.g. 8° of the surface normal with respect to the optical axis. This causes the ubiquitous back reflections to be directed away from the fibre's optical axis into the cladding. By tilting the entrance and exit windows in a similar fashion, the same effect can be achieved in the field of intraoral devices. An advantage of the tilted surfaces of the first and second optical interfaces 46, 48 is that they do not need to be anti-reflection coated, which again lowers the production costs and at the same time makes them more robust with respect to mechanical cleaning as typically anti-reflection coatings can be damaged easily.

Figure 6:
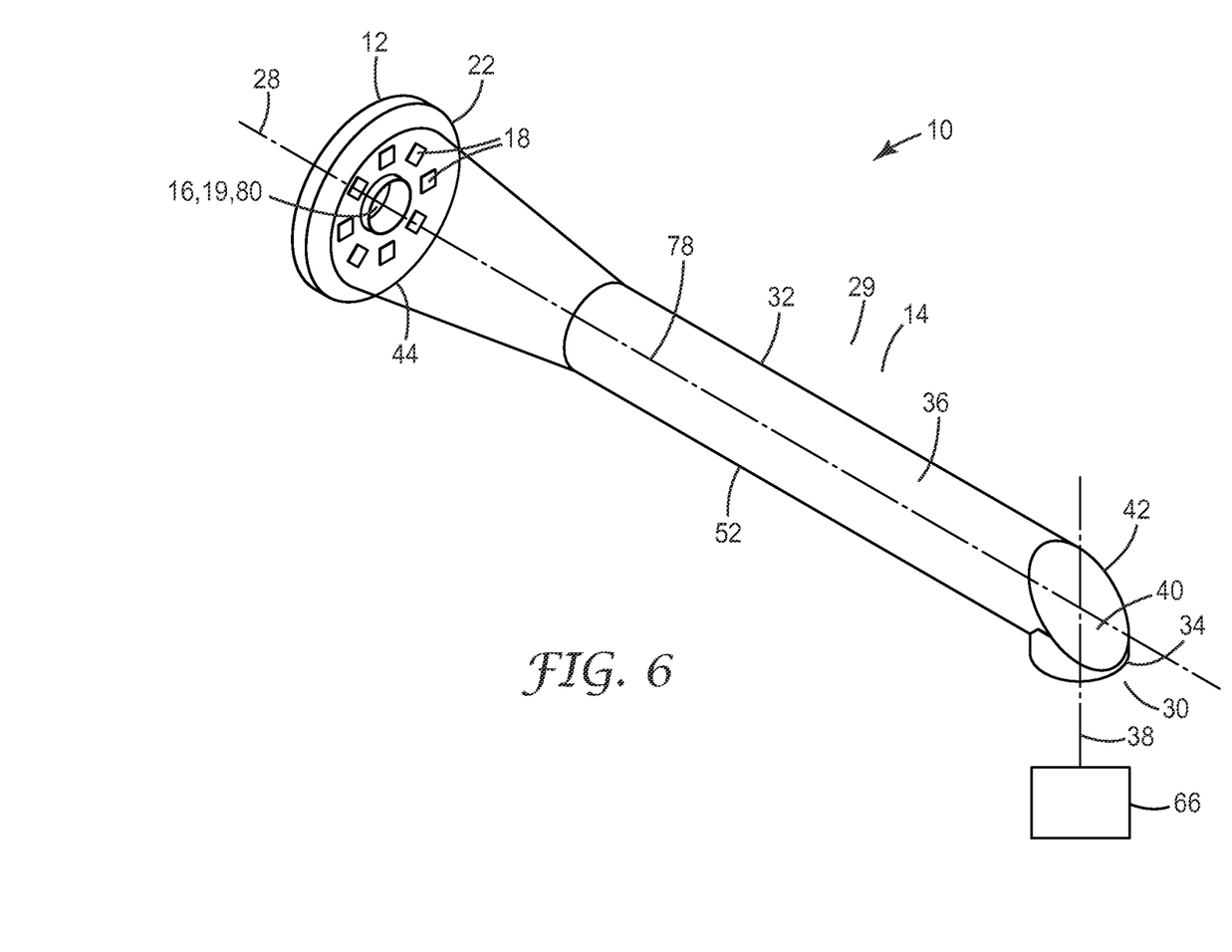
FIG. 6 shows a partial perspective view of an intraoral imaging and illumination apparatus according to a sixth embodiment of the present invention.

FIG. 6 shows a partial perspective view of an intraoral imaging and illumination apparatus 10 according to a sixth embodiment. Hereinafter, only differences from the previous embodiments are described and like constructional members are indicated by like reference signs.

The intraoral imaging and illumination apparatus 10 of the sixth embodiment is substantially based on the first embodiment. According to the intraoral imaging and illumination apparatus 10 of the sixth embodiment, the illumination device 18 is arranged offset with respect to the first longitudinal axis 28. For example, the illumination device 18 comprises a plurality of LEDs which are arranged coaxially with respect to the first longitudinal axis 28. For example, the LEDs of the illumination device 18 are arranged circularly around the first longitudinal axis 28 representing the optical path of the imaging device 16.

The LEDs of the illumination device 18 are tilted with respect to a central axis 78. The central axis 78 is an axis around which the LEDs of the illumination device 18 are arranged. With other words, the LEDs are arranged such that they emit light towards a common or central axis 78. Particularly, the LEDs of the illumination device 18 are tilted such that the central axis 78 extends through the front portion 14. With other words, the LEDs of the illumination device 18 are tilted towards the front portion 14 and the leading end 30 thereof. The position and number of LEDs may be determined such that always two LEDs are opposed to one another with the central axis 78 therebetween. Thus, the LEDs may be symmetrically arranged around the central axis 78. For example, the LEDs are evenly spaced apart from one another around the central axis 78.

The central axis 78 may overlap with the second longitudinal axis 36 of the proximal section 32 of the front portion 14. Additionally, the central axis 78 may overlap with the first longitudinal axis 28. The central axis 78 also overlaps with the optical path of the imaging device 16. Particularly, the central axis 78 extends through a camera objective aperture 80 of the camera 19 of the imaging device 16. For example, the LEDs of the illumination device 18 may be circularly arranged around the camera objective aperture 80.

A basic idea of the intraoral imaging and illumination apparatus 10 of the sixth embodiment is to superimpose a curing light onto a camera image via an optical light guide 29 of the front portion 14 made either from a hollow tube or a solid rod, shaped such that light is coupled in under an angle and guided towards the leading end 30 of the front portion 14. The light can be generated by a number of LEDs positioned e.g. radially around a central camera imager. Other geometries of the LEDs of the illumination device 18, e.g. quadratic or cross-like positioning, are conceivable and influence only the positioning of the LEDs. The intraoral imaging and illumination apparatus 10 of the sixth embodiment has the advantages of a reduced optical complexity combined with off-the-shelf camera optics and most importantly the total elimination of back reflection or stray light artefacts in the camera image resulting from the parallel illumination.

The fact that the design allows for the placement of several LED's significantly reduces the intensity requirements for the individual LEDs and easily compensates any additional light losses which occur inside the removable front portion 14 formed as a light guide 29. This potentially widens the selection of applicable LEDs.

The illumination apparatus 10 of the sixth embodiment solves some specific problems of current dental devices as will be explained in further detail below. Current dental procedures include visible light curing of restorative materials with e.g. blue light from an LED based handheld device. The very bright curing light is hard to look at and therefore can cause the operator to avert his/her eyes. Manual shielding of the light is cumbersome and often insufficient, leading to unwanted process variations as the position of the tip of the curing device can shift due to patient or operator movement and lack of direct feedback for compensation. A typical curing procedure takes about 20 seconds and due to the errors described above the restorative material can either be cured partially or it can be irradiated too much. Overall this leads to a significant reduction in the lifetime of dental restorations.

These problems are solved by the intraoral imaging and illumination apparatus 10 of the sixth embodiment in that the dentist is supported via an imaging device 16, e.g. a digital camera, which shows the irradiated region. Thereby, the process stability can be increased as the operator receives a direct visual feedback on the position of the curing light. Further, such a camera is combined with a curing light. It is preferred to design the intraoral imaging and illumination apparatus 10 of the sixth embodiment with a superposition of both the optical paths of the imaging device 16 and the light sources of the illumination device 18 via an axially symmetric placement of the light sources around at least parts of the imaging device 16.

The light guiding efficiency can be further increased by collimating the light sources of the illumination device 18, tilting the light sources of the illumination device 18 with respect to a central axis 78 of the intraoral imaging and illumination apparatus 10, coating the first and second optical interfaces 46, 48 with anti-reflection coatings and/or using higher reflectivity surfaces of the outer tube 50 and the inner tube 52, e.g. multilayer optical films, provide less losses for the guided light.

An additional advantage of this concept is that compared to designs in which all active components, i.e. LEDs and camera, are located at the distal end of the wand, the heat can be managed more efficiently due to the increased available space. In the proposed design, the light sources of the illumination device 18 and the camera 19 of the imaging device 16 reside inside the wider rear portion 12 outside of the pencil-like front portion 14. The front portion 14 and the tip thereof are preferably slim as they are inserted into the patient's mouth. Furthermore, the ability to include a larger, e.g. metal, heat sink underneath the LEDs reduces the heating of the imaging device 16 and thereby reduces the electronic noise or alternatively the temperature tolerances of the camera 19 of the imaging device 16.

Figure 7:
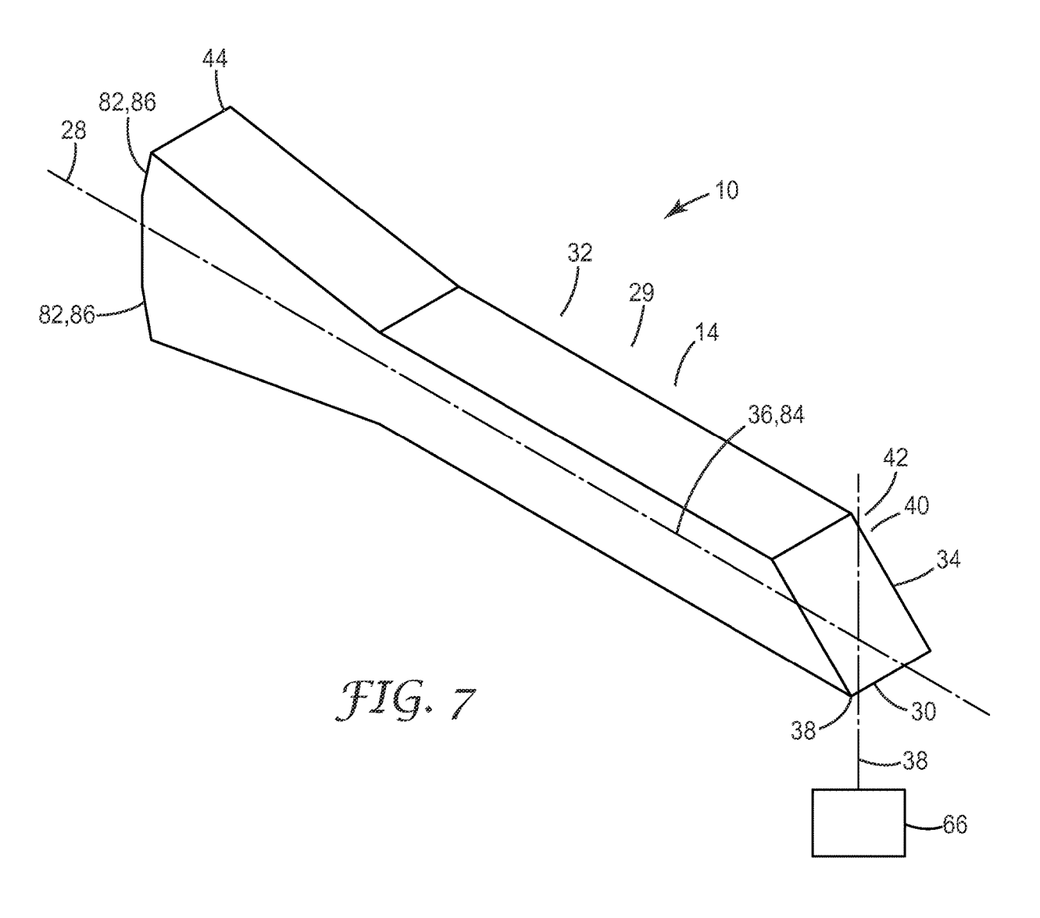
FIG. 7 shows a partial perspective view of an intraoral imaging and illumination apparatus according to a seventh embodiment of the present invention.

FIG. 7 shows a partial perspective view of an intraoral imaging and illumination apparatus 10 according to a seventh embodiment. Hereinafter, only differences from the previous embodiments are described and like constructional members are indicated by like reference signs.

The intraoral imaging and illumination apparatus 10 of the seventh embodiment is substantially based on the sixth embodiment. According to the intraoral imaging and illumination apparatus 10 of the seventh embodiment, the front portion 14 is formed as a solid light guide 29 adapted to reflect light. The solid light guide 29 is made of at least one material adapted to guide light. For example, the solid light guide 29 is made at least partially of plastics or glass. The light guide 29 comprises a rectangular cross-section. It is to be noted that this cross-section is taken perpendicular to the second longitudinal axis 36. Further, light guide 29 comprises light coupling elements 82. The light coupling elements 82 are tilted with respect to a central axis 84. The light coupling elements 82 are provided by means of angled interfaces 86 above and below the central axis 84 of the light guide 29. The light coupling elements 82 are tilted towards the leading end 30 of the front portion 14. Similar as the previous embodiments, the solid light guide 29 comprises the first optical interface 46 and the second optical interface 48. The first optical interface 46 and the second optical interface 48 of the seventh embodiment are not glass windows but surfaces of the solid light guide 29 which are transparent for light.

According to the intraoral imaging and illumination apparatus 10 of the seventh embodiment, the light guiding efficiency is further increased by using the solid light guide 29 based on lossless total internal reflection. The solid light guide 29 may be either fixed inside a protective case (not shown in detail) or coated to prevent coupling losses introduced by physical contact with the patient's mouth, saliva or the like. Similar light coupling elements could be added in the direction of the central axis 84 yielding e.g. a cross-like shape. A rectangular footprint of the coupling elements is also possible.

What is claimed is:

1. An intraoral imaging and illumination apparatus comprising:
    a rear portion comprising an imaging device and an illumination device;
    a beam splitter disposed in the rear portion; and
    a front portion removably connected to the rear portion, wherein
        the front portion is formed as a light guide,
        the illumination device is adapted to couple light into the front portion and towards a leading end of the front portion opposite the rear portion so as to illuminate a first object,
        the imaging device is adapted to image the first object, and
        the beam splitter is adapted to split light emitted by the illumination device and incident thereon into a first fraction directed towards the front portion and a second fraction directed towards a second object different from the first object.

2. The intraoral imaging and illumination apparatus of claim 1, wherein the front portion is adapted to reflect light coupled into the front portion from the illumination device.

3. The intraoral imaging and illumination apparatus of claim 1, wherein the rear portion defines a first longitudinal axis, wherein the imaging device or the illumination device is axially arranged with respect to the first longitudinal axis.

4. The intraoral imaging and illumination apparatus of claim 3, wherein the imaging device or the illumination device is arranged offset with respect to the first longitudinal axis.

5. The intraoral imaging and illumination apparatus of claim 1, wherein the second object is disposed within the rear portion.

6. The intraoral imaging and illumination apparatus of claim 5, wherein the imaging device is adapted to image the second object.

7. The intraoral imaging and illumination apparatus of claim 1, further comprising an automated focusing device disposed within the rear portion, wherein the automated focusing device is configured to switch focus between the first object and the second object.

8. The intraoral imaging and illumination apparatus of claim 1, wherein the front portion comprises a proximal section facing the rear portion and a distal section facing away from the rear portion, wherein the proximal section and the distal section are angled relative to one another, wherein the front portion comprises a reflecting device disposed at a transition from the proximal section to the distal section.

9. The intraoral imaging and illumination apparatus of claim 8, wherein the proximal section defines a second longitudinal axis, wherein the first longitudinal axis and the second longitudinal axis overlap when the front portion is connected to the rear portion.

10. The intraoral imaging and illumination apparatus of claim 9, wherein the front portion comprises a rear end facing the rear portion, wherein a first optical interface is arranged at the rear end, wherein the first optical interface is tilted with respect to the second longitudinal axis.

11. The intraoral imaging and illumination apparatus of claim 8, wherein the distal section defines a third longitudinal axis, wherein the third longitudinal axis is angled with respect to the second longitudinal axis, wherein a second optical interface is arranged at the leading end of the front portion, wherein the second optical interface is tilted with respect to the third longitudinal axis.

12. The intraoral imaging and illumination apparatus of claim 1, wherein the illumination device comprises at least one LED or laser.

13. The intraoral imaging and illumination apparatus of claim 12, further comprising at least one collimating device adapted to collimate light emitted from the at least one LED or laser.

14. The intraoral imaging and illumination apparatus of claim 12, wherein the at least one LED or laser are tilted with respect to a central axis.

15. The intraoral imaging and illumination apparatus of claim 1, wherein the illumination device simultaneously illuminates the first object and the second object.

16. An intraoral imaging and illumination apparatus comprising:
a rear portion comprising an imaging device and an illumination device;
a beam splitter or dichroic mirror disposed in the rear portion;
an automated focusing device disposed within the rear portion; and
a front portion removably connected to the rear portion, wherein:
the front portion is formed as a light guide,
the illumination device is adapted to emit light through the beamsplitter,
the beam splitter or dichroic mirror is adapted to split light emitted by the illumination device and incident thereon into a first fraction directed towards the front portion and a second fraction directed towards a color standard or palette of color references,
the first portion of light couples into the front portion and towards a leading end of the front portion opposite the rear portion so as to illuminate a first object,
the automated focusing device is configured to switch focus between the first object and the color standard or palette of color references, and
the imaging device is adapted to image the first object and the color standard or palette of color references, depending on the focus of the automated focusing device.

* * * * *

UNITED STATES PATENT AND TRADEMARK OFFICE
CERTIFICATE OF CORRECTION

PATENT NO. : 10,271,720 B2
APPLICATION NO. : 15/127622
DATED : April 30, 2019
INVENTOR(S) : Fink et al.

Page 1 of 1

It is certified that error appears in the above-identified patent and that said Letters Patent is hereby corrected as shown below:

In the Specification

Column 1
Line 44, delete "and or" and insert -- and/or --, therefor.

Column 8
Line 58, after "64" insert -- . --.

Column 13
Line 62, after "artefacts" insert -- . --.

Signed and Sealed this
Tenth Day of March, 2020

Andrei Iancu
*Director of the United States Patent and Trademark Office*